(12) United States Patent
Peng et al.

(10) Patent No.: US 10,219,989 B2
(45) Date of Patent: Mar. 5, 2019

(54) SPECIAL EFFECTS WITH MIXTURES OF INTERFERENCE PIGMENTS

(71) Applicant: MERCK PATENT GMBH, Darmstadt (DE)

(72) Inventors: Qinyun Peng, Yorktown Heights, NY (US); Philip Linz, Croton-Hudson, NY (US)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/082,918

(22) Filed: Mar. 28, 2016

(65) Prior Publication Data

US 2016/0206530 A1 Jul. 21, 2016

Related U.S. Application Data

(63) Continuation of application No. 12/344,857, filed on Dec. 29, 2008, now abandoned, which is a continuation of application No. 11/217,675, filed on Sep. 2, 2005, now abandoned.

(60) Provisional application No. 60/606,503, filed on Sep. 2, 2004.

(51) Int. Cl.

| *A61K 8/29* | (2006.01) |
| *C09D 11/037* | (2014.01) |
| *A61K 8/19* | (2006.01) |
| *A61K 8/26* | (2006.01) |
| *A61Q 1/02* | (2006.01) |
| *C09C 1/00* | (2006.01) |
| *A61K 8/25* | (2006.01) |
| *C09D 17/00* | (2006.01) |
| *C08K 5/00* | (2006.01) |

(52) U.S. Cl.
CPC .............. *A61K 8/29* (2013.01); *A61K 8/19* (2013.01); *A61K 8/25* (2013.01); *A61K 8/26* (2013.01); *A61Q 1/02* (2013.01); *C09C 1/0015* (2013.01); *C09C 1/0021* (2013.01); *C09C 1/0024* (2013.01); *C09C 1/0039* (2013.01); *C09C 1/0081* (2013.01); *C09D 11/037* (2013.01); *C09D 17/007* (2013.01); *C09D 17/008* (2013.01); *A61K 2800/436* (2013.01); *A61K 2800/592* (2013.01); *C01P 2004/54* (2013.01); *C01P 2004/61* (2013.01); *C01P 2006/60* (2013.01); *C08K 5/0041* (2013.01); *C09C 2220/10* (2013.01)

(58) Field of Classification Search
CPC ........ A61K 2800/436; A61K 2800/592; A61K 8/19; A61K 8/25; A61K 8/26; A61K 8/29; A61Q 1/02; C01P 2004/54; C01P 2004/61; C01P 2006/60; C08K 5/0041; C09C 1/0015; C09C 1/0021; C09C 1/0024; C09C 1/00
See application file for complete search history.

(56) References Cited

U.S. PATENT DOCUMENTS

| 3,929,501 | A | 12/1975 | Dunn |
| 4,200,474 | A | 4/1980 | Morris |
| 5,451,632 | A | 9/1995 | Okumura et al. |
| 5,565,025 | A | 10/1996 | Schraml-Marth |
| 5,626,661 | A | 5/1997 | Schmidt et al. |
| 5,753,371 | A | 5/1998 | Sullivan et al. |
| 5,780,018 | A | 7/1998 | Collins et al. |
| 6,045,914 | A | 4/2000 | Sullivan et al. |
| 6,060,071 | A | 5/2000 | Motitschke et al. |
| 6,419,736 | B1 | 7/2002 | Pfaff et al. |
| 6,517,628 | B1 | 2/2003 | Pfaff et al. |
| 6,596,070 | B1 | 7/2003 | Schmidt et al. |
| 6,875,262 | B1 | 4/2005 | Zimmermann et al. |
| 2004/0123778 | A1* | 7/2004 | Bagala, Sr. .......... A61K 8/0254 106/415 |
| 2004/0191198 | A1* | 9/2004 | Hochstein ................. A61K 8/26 424/63 |
| 2005/0220741 | A1 | 10/2005 | Dumousseaux |
| 2006/0013838 | A1* | 1/2006 | Peng .................... A61K 8/25 424/401 |

FOREIGN PATENT DOCUMENTS

| JP | 2001/11340 | 1/2001 |
| WO | 1999/20695 | 4/1999 |
| WO | 1999/46336 | 9/1999 |
| WO | 2002/090448 | 11/2002 |
| WO | 2003/006558 | 1/2003 |

* cited by examiner

*Primary Examiner* — Shuangyi Abu Ali
(74) *Attorney, Agent, or Firm* — Millen, White, Zelano and Branigan, P.C.

(57) ABSTRACT

A method of producing mixtures of interference pigments having special effects comprises mixing at least one large particle size interference pigment with at least one normal size interference pigment of predetermined colors and in proportions desired to obtain a unique effect.

7 Claims, No Drawings

SPECIAL EFFECTS WITH MIXTURES OF INTERFERENCE PIGMENTS

This application is a continuation of U.S. patent application Ser. No. 12/344,857, filed Dec. 29, 2008 which is a continuation of U.S. patent application Ser. No. 11/217,675, filed Sep. 2, 2005, now abandoned, which claims the benefit of the filing date of U.S. Provisional Application Ser. No. 60/606,503 filed Sep. 2, 2004 which is incorporated by reference herein.

CROSS REFERENCE TO RELATED APPLICATION

This application is related to Applicants', entitled COSMETIC POWDER COMPOSITIONS HAVING LARGE PARTICLE SIZE COLOR EFFECT PIGMENTS filed Jul. 13, 2004, U.S. application Ser. No. 10/889,003.

SPECIFICATION

This provisional application relates to mixtures of interference pigments having novel color effects, and to articles and compositions containing such pigments, especially cosmetic compositions, and to methods of producing such mixtures and products.

Interference pigments sometimes called pearlescent or iridescent pigments, have a long history including but not limited to natural pigments for cosmetic uses in early Egypt, the production of artificial pearls in France in the 17th century, and the emergence of titanium dioxide coated mica in the 1960's for many applications, not only in cosmetics of all types, but also for industrial uses for example, for providing decorative bottles, and especially for the large scale production of pearlescent paints for the automotive industry. Descriptions of interference pigments are found in patents and pertinent literature, e.g. Pearl Lustre Pigments, Marsch and Wiegand (translation J H Steele) 1992, verlag moderne industrie AG & Co., D8910 Landsberg/Lech, Germany. Special color effects have been developed, based on particular substrates and coatings, for example, the relatively new multi-layer interference pigments and, color travel pigments, which change colors depending upon the viewing angle of the observer.

Acknowledging the extensive and ongoing research conducted in this field, objects of this invention include new pigment mixtures and methods of producing same. Upon further study of the specification and dependent claims, other objects and advantages of the invention will become apparent.

To achieve these objects, there is provided a method of producing mixtures of pigments comprising at least one normal size interference pigment with at least one large particle size interference pigment. A large particle size interference pigment (hereinafter synonymously referred to as glitter pigment) has a median particle size (D50) of more than 40 µm, especially more than 60 µm. The maximum D50 particle size is about 150 µm, preferably 60-120 µm, but it should be noted that glitter pigments may have a particle size of up to 250 µm. Conversely, normal (synonymously referred to as smaller) particle size interference pigments have a D50 below 40 µm, especially below 30 µm, but in general should not be less than 15 µm. It was unexpected that the resultant color appearance of the mixture of interference pigments was not only dependent on the color of each individual pigment but also on its particle size.

Heretofore, the general color mixing rule for interference pigments was additive mixing because the reflected light portions from each pigment are added together, e.g. a mixture of blue and yellow is white and the mixture of green and red is yellow. A discovery of the present invention is that by adjusting the particle size of different colored interference pigments that unusual effects are obtained. The particle size difference between normal and large interference pigments should be sufficiently significant to minimize the color cancellation effect, for example the difference in D50 values between the normal particle size and the large particle size is preferably about 40-80 µm. The specific difference will be dependent on the proportions of the normal and large particle size interference pigments in the mixture as well as the specific colors of each particle size. If the D50 of the normal particle size interference pigment is too small or the proportion is too high, the luster of the large particle size interference pigment will be significantly reduced by virtue of the overwhelming covering power and light scattering power of the normal particle size pigment. (The surface area of a pigment may be used as a reference to evaluate the suitability and to optimize color mixing.)

In order to obtain the particular effects of the invention, the intensity of the color of the large particle size pigment, plays an important role in color mixing, but it is the very size of the large particle size interference pigment which is essential to the success of the invention. It has been discovered, to the contrary, that if one blends a normal particle size interference pigment with an interference pigment having a smaller D50 than that of normal size pigment, the unusual color effects are not obtained.

To produce the desired particle size, conventional methods are employed, for example, by sedimentation.

The chemical nature of the individual interference pigments, aside from particle size can be varied widely, from substrate-free pigments, to substrate-based pigments of monolayer or multilayer metal oxide coating(s), all well known in the pertinent general and patent literature. Particularly special effects occur when the normal size pigment and/or the large size pigment is a color travel pigment.

Possible Compositions of the Interference Pigments:

Suitable base substrates for substrate-based pigments include, but are not limited to transparent flake-form substrates. Preferred substrates are phyllosilicates. Particularly suitable are natural and/or synthetic mica, glass flakes, $SiO_2$ flakes, aluminum oxides, sericite, talc, kaolin, flake-form iron oxides or $TiO_2$ flakes, BiOCl or other comparable materials.

The size of the base substrates can be matched to the particular application. In general, the flake-form substrates have a thickness of between 0.05 and 5 µm, in particular between 0.1 and 4.5 µm. The size in the other two directions is usually between 1 and 550 µm, preferably between 2 and 300 µm, and in particular between 5 and 250 µm. As known by those skilled in the art, the thickness of the individual layers on the base substrate is essential for the optical properties of the pigment. The aspect ratio (ratio of surface dimension to thickness of an object) is preferably about 1-500, especially 40-350.

The interference pigments according to the invention have high and/or low refractive-index layer(s) on top of the substrate. The high-refractive-index layer(s) have a refractive index of $n>1.8$, preferably of $n \geq 2.0$. The high refractive-index layers preferably comprise $TiO_2$, $Fe_2O_3$, $Fe_3O_4$, $ZrO_2$, $SnO_2$, ZnO, BiOCl, $Cr_2O_3$, $CeO_3$, molybdenum oxides, CoO, $Co_3O_4$, $VO_2$, $V_2O_3$, NiO, $V_2O_5$, CuO, $Cu_2O$, $Ag_2O$, $CeO_2$, $MnO_2$, $Mn_2O_3$, $Mn_2O_5$, titanium oxynitrides, pseudobrookite, ilmenite, as well as titanium nitride, $MoS_2$, $WS_2$ or mixtures or combinations thereof. The $TiO_2$ here can be in the rutile or anatase modification, preferably in the rutile modification.

Suitable low-refractive-index materials ($n \leq 1.9$) are preferably metal oxides or the corresponding oxide hydrates, such as, for example, $SiO_2$, $Al_2O_3$, $AlO(OH)$, $B_2O_3$, $MgF_2$, $MgSiO_3$ or a mixture of the said metal oxides.

Particularly interesting interference pigments have the following layer sequences:
   substrate+$TiO_2$
   substrate+$Fe_2O_3$
   substrate+$Fe_3O_4$
   substrate+$Cr_2O_3$
   substrate+—TiO suboxide
   substrate+$TiO_2$+$Fe_2O_3$
   substrate+$TiO_2$+$SiO_2$+$TiO_2$
   substrate+$TiO_2$/$Fe_2O_3$
   substrate+$TiO_2$/$Fe_2O_3$+$SiO_2$+$TiO_2$/$Fe_2O_3$
   substrate+$TiO_2$/$Fe_2O_3$+$SiO_2$+$TiO_2$
   substrate+$TiO_2$+$SiO_2$+$TiO_2$/$Fe_2O_3$
   substrate+$Fe_2O_3$+$SiO_2$+$TiO_2$/$Fe_2O_3$
   substrate+$TiO_2$/$Fe_2O_3$+$SiO_2$+$Fe_2O_3$
   substrate+$TiO_2$+$SiO_2$+$Fe_3O_4$
   substrate+$Fe_3O_4$+$SiO_2$+$TiO_2$ The pigments according to the invention can be prepared relatively easily by the deposition of materials of high- and/or low-refractive-index, having precisely defined thickness and a smooth surface on the finely divided, flake-form substrates.

The metal-oxide layers are preferably applied by wet-chemical methods. Methods of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or in further patent documents and other publications known to the person skilled in the art. For example, in wet coating, the substrate particles are suspended in water, and one or more hydrolyzable metal salts are added at a pH which is suitable for hydrolysis and which is selected so that the metal oxides or metal oxide hydrates are precipitated directly onto the flakes without secondary precipitations occurring. The pH is usually kept constant by simultaneous metered addition of a base or acid. The pigments are subsequently separated off, washed and dried and, if desired, calcined, where the calcination temperature can be optimized with respect to the coating present in each case. In general, the calcination temperatures are between 250 and 1000° C., preferably between 350 and 900° C. If desired, the pigments can be separated off after application of individual coatings, dried and, if desired, calcined and then re-suspended for the deposition of the further layers.

The coating may furthermore also take place in a fluidized-bed reactor by gas-phase coating, it being possible, for example, to use correspondingly the methods proposed in EP 0 045 851 and EP 0 0106 235 for the preparation of pearlescent pigments.

The production of Ti suboxide or $Fe_3O_4$ layers can be carried out, for example, by reduction of the $TiO_2$ layer using ammonia, hydrogen and also hydrocarbons and hydrocarbon/ammonia mixtures, as described, for example, in EP-A-0 332 071, DE 199 51 696 A1 and DE 199 51 697 A1. The reduction is preferably carried out in a forming-gas atmosphere (92% of $N_2$/8% of $H_2$ or 96% of $N_2$/4% of $H_2$). The reduction is generally carried out at temperatures of 250-1000° C., preferably 350-900° C. and in particular 500-850° C.

The hue of the pigments can be varied within conventionally broad limits by a choice of the coating amounts and/or the layers resulting therefrom. Fine tuning for a certain hue can be achieved by utilizing visual or optical measurement technology.

In order to increase the light, water and weather stability, it is frequently advisable, depending on the area of application, to subject the finished pigment to post-coating or post-treatment. Suitable post-coatings or post-treatments are, for example, the processes described in German Patent 22 15 191, DE-A 31 51 354, DE-A 32 35 017, DE-A 33 34 598, DE 40 30 727 A1, EP 0 649 886 A2, WO 97/29059, WO 99/57204 and U.S. Pat. No. 5,759,255. This post-coating further increases the chemical stability of the pigments or simplifies the handling of the pigment, in particular the incorporation into various media. In order to increase the light, water and weather stability, dispersibility and/or compatibility with the application media, it is possible for functional coatings of $Al_2O_3$ or $ZrO_2$ or mixtures thereof or mixed phases to be applied to the pigment surface. Furthermore, organic or combined organic/inorganic post-coatings may be employed for example with silanes, as described, for example, in EP 0090259, EP 0 634 459, WO 99/57204, WO 96/32446, WO 99/57204, U.S. Pat. No. 5,759,255, U.S. Pat. No. 5,571,851, WO 01/92425 or in J. J. Ponjee, Philips Technical Review, Vol. 44, No. 3, 81 ff. and P. H. Harding J. C. Berg, J. Adhesion Sci. Technol. Vol. 11 No. 4, pp. 471-493. Also, the interference pigments can advantageously be used in blends with organic dyes, organic pigments or other pigments. They can be mixed in any ratio with commercially available pigments and fillers.

In general, all types of interference pigments can be used. More examples of such pigments include but are not limited to those described in published U.S. patent application Ser. No. 10/608,563, by Cristoph Schmidt et al. filed Jun. 30, 2003, as well as to those described in the patents and literature cited therein, e.g. U.S. Pat. No. 4,434,010, JP H7-759, U.S. Pat. No. 3,438,796, U.S. Pat. No. 5,135,812, DE 44 05 494, DE 44 37 753, DE 195 16 181 and DE 195 15 988, DE 196 18 565, DE 197 46 067 and in the literature, for example in EURO COSMETICS, 1999, No. 8, p. 284.

It goes without saying that, for the various applications, the mixture of interference pigments can also advantageously be used in the form of a mixture with organic dyes, organic pigments or other pigments, such as, for example, transparent and opaque white, coloured and black pigments, and with flake-form iron oxides, organic pigments, holographic pigments, LCPs (liquid crystal polymers) and conventional transparent, coloured and black lustre pigments based on metal oxide-coated mica and $SiO_2$ flakes, etc. The interference pigment mixture according to the invention can be mixed in any ratio with commercially available pigments and fillers. Preferred fillers are for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, flake-form, spherical or needle-shaped in accordance with requirements.

The pigments according to the invention are compatible with a multiplicity of color systems, preferably from the area of cosmetics and personal care products, paints, coatings and printing inks. It is important to appreciate that the present invention is applicable for all applications where a decorative effect is desired.

As merely one example among all the applications described in patents and pertinent literature, the compositions of this invention can be used in the form of a liquid cosmetic formulation for application to nails or skin. Examples of such cosmetic formulation include but are not limited to: nail lacquer, bath oil, shower gel, body wash, shampoos, conditioner, liquid soap, skin cleanser, hand sanitizer, sunless tanning foam and lotion, skin cream and lotion, body lotion, liquid eye make up, liquid foundation, hair gel, hydrogel, styling gel, lip products, such as lip gloss, lipstick. Also, the composition of this invention can be used in formulations, such as for example, foundation (liquid and stick), face makeup such as cream-to-powder, eye highlighter, eye pencil, bronzing stick, blusher, powder makeup, lip powder, face powder, body powder and, bronzing powder etc.

The formulations comprising the interference pigment mixture according to the invention can belong to the lipophilic, hydrophilic or hydrophobic type. In the case of heterogeneous formulations having discrete aqueous and non-aqueous phases, the interference pigment mixtures according to the invention may in each case be present in only one of the two phases or alternatively distributed over both phases.

The invention relates, in particular, to formulations which, besides the interference pigment mixture according to the invention, comprise at least one constituent selected from absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilisers, dyes, humectants, film formers, odour substances, flavour substances, insect repellents, preservatives, anticorrosion agents, cosmetic oils, solvents, oxidants, vegetable constituents, buffer substances, reducing agents, surfactants, propellent gases, opacifiers, UV filters and UV absorbers, denaturing agents, viscosity regulators, perfume and vitamins.

The above or following description of the multitude of pigments that can be used is not intended to be exclusive since there are a wide variety of interference pigments that have been developed and which will be developed in the future. This invention is based on a finding that the mixture of a large particle size interference pigment with a small particle size interference pigment can yield highly unusual effects, especially when using non-complementary colors.

As to the proportions of the normal and large particle size interference pigments, it is contemplated that all proportions will be utilizable, for example in part by weight 99:1 to 1:99, especially 75:25 to 25:75, depending on the specific particle size of each type of pigment, the color of each type of pigment, the D50 difference in particle sizes, etc., in order to obtain the desired color effect.

For details of other interference pigments, reference is invited to patents and the pertinent literature. Irrespective of the nature of the individual pigments, the present invention can be utilized by merely mixing at least one large particle size pigment with at least one normal size pigment of a different color.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The following examples show the results of mixing normal and/or large particle size interference pigments (D50>60 μm). For convenience, these large particle size interference pigments are also called glitter interference pigments in the examples. For Timiron® Super Color pigments and Timiron® Splendid Color pigments, their particle size range is 10-60 μm and D50 is 18-25 μm. To demonstrate the color mixing effect more effectively, mixtures are drawdowned on Leneta cards respectively in a nitrocellulose lacquer. The color over black is photographed at the luster angle to show the luster of the mixture.

As a disclaimer, it is to be noted that one or more examples may have not been actually conducted.

EXAMPLE 1

Mixing two interference pigments of complementary colors (with the same particle size range) in 1 to 1 ratio by weight.

When Timiron® Super Blue is blended with Timiron® Super Gold, the interference colors of the blue and gold pigments are no longer visible due to color cancellation (according to the color mixing rule). On the other hand, when experimental glitter interference blue and gold pigments (both D50 about 74 μm) are mixed together, the blue and gold luster colors of pigment particles are discernable macroscopically. This mixture renders the so called multicolor effect.

Similar results are obtained for the mixtures of green and red interference pigments in normal or large particle size. Therefore, a multi-color effect can be created by mixing large particle size interference pigments.

EXAMPLE 2

Mixing two interference pigments of complementary colors (one with large particle size and the other with normal particle size) in 1 to 1 ratio by weight.

The luster color of the mixture depends on the color choice of large particle size pigments and is shown below.

A first mixture consists of experimental glitter interference gold (D50~74 μm) and Timiron® Splendid Blue. Since the intensity of interference gold color is normally higher than that of blue, the sparkling gold pigment particles can be seen clearly in the environment of smooth blue luster pigment. This mixture has a very attractive color and no significant color cancellation is observed. In the second case, when experimental glitter interference blue (D50~74 μm) is blended with Timiron® Splendid Gold, we are able to see blue luster from some of the pigment particles, but the color is quite dull when compared to the intense interference gold color. This mixture gives a less impressive color.

The same is true again for blending red and green interference pigments of normal and large particle sizes. The luster color of the mixture of experimental glitter interference red (D50~74 μm) and Timiron® Splendid Green (D50~22 μm) is rather different from that of the mixture of experimental glitter interference green (D50~74 μm) and Timiron® Splendid Red (D50~22 μm).

The examples show that it is possible to create a product consisting of complementary interference colors by mixing a large particle size pigment with a normal size pigment of complementary color to minimize the color cancellation. However, this cannot be accomplished by mixing different D50 fractions of normal particle size pigments. Additionally, the choice of color for the large particle size pigment is important.

EXAMPLE 3

Mixing two interference pigments of non-complementary colors (one with large particle size and the other with normal particle size) in 1 to 1 ratio by weight.

Some unexpected highly attractive color effects are generated by this type of mixing. When experimental glitter interference red (D50~74 μm) and Timiron® Splendid Blue (D50~22 μm) are mixed together, the luster color of the mixture becomes bluish magenta and is surprisingly striking. In addition, the sparkling luster of the experimental glitter red interference pigment can be seen clearly as well. Whereas, when experimental glitter interference blue (D50~74 μm) is mixed with Timiron® Splendid Red, the color effect of the mixture is still red, but less vivid and no magenta luster color is developed.

This example demonstrates the importance of choosing the color of the large particle size pigment in order to achieve a specific color effect.

The compositions of the various pigments referred to in the above examples are tabulated as follows:

| Description | INCI name | D50 (μm) | Particle Size Range (μm) |
|---|---|---|---|
| Timiron Splendid Blue | titanium dioxide, mica, silica | 18~25 | 10~60 |
| Timiron Splendid Gold | titanium dioxide, mica, silica | 18~25 | 10~60 |
| Timiron Splendid Green | titanium dioxide, mica, silica | 18~25 | 10~60 |
| Timiron Splendid Red | titanium dioxide, mica, silica | 18~25 | 10~60 |
| Experimental Glitter Interference Blue | mica, titanium dioxide | 60~100 | 10~150 |
| Experimental Glitter Interference Gold | mica, titanium dioxide | 60~100 | 10~150 |
| Experimental Glitter Interference Green | mica, titanium dioxide | 60~100 | 10~150 |
| Experimental Glitter Interference Red | mica, titanium dioxide | 60~100 | 10~150 |

In substantially the same manner, other mixtures are producible, as below, the percentage being in percent by weight of each pigment of a mixture in a nitrocellulose lacquer.

1. 2% Colorona® Glitter Copper/2% Timiron® Splendid Green: glitter copper particle is clearly visible over a green background
2. 2% Large particle size color travel (Green blue/Lilac)/2% Xirona® Magic Mauve: the color travel effect of Xiron® Magic Mauve is dominating.
3. 2% Large particle size color travel (Green blue/Lilac)/2% Xirona® Nordic Sunset: the color travel effect of Xirona® Nordic Sunset is dominating.
4. 2% Large particle size color travel (Red/Gold)/2% Experimental Glitter Interference Blue: the color travel effect is unchanged and the blue background is clearly visible, very interesting color effect.
5. 2% Large particle size color travel (Red/Gold)/1% Experimental Glitter Interference Blue: similar effect as 4.
6. 2% Xirona® Volcanic Fire/2% Experimental Glitter Interference Blue: color travel effect from Xirona Volcanic Fire is modified.
7. 2% Xirona® Volcanic Fire/1% Experimental Glitter Interference Blue: similar as 6, except the color travel effect was changed less dramatically.
8. 2% Large particle size color travel (Red/Gold)/2% Experimental Glitter Interference Green: color travel effect remains, multi-color effect is created, very interesting color effect.
9. 2% Large particle size color travel (Red/Gold)/1% Experimental Glitter Interference Green: similar as 8
10. 2% Xirona® Volcanic Fire/2% Experimental Glitter Interference Green: color travel effect from Xirona® Volcanic Fire is greatly diminished.
11. 2% Xirona® Volcanic Fire/1% Experimental Glitter Interference Green: similar as 10.
12. 2% Experimental Glitter Interference Red/2% Timiron® Splendid Gold: The gold color overwhelms the red.
13. 2% Experimental Glitter Interference Red/0.5% Timiron® Splendid Gold: interesting color effect.
14. 2% Reflecks™ Beams of Blue/2% Reflecks™ Gleams of Gold: similar effect as shown in example 1.
15. 2% Reflecks™ Beams of Blue/2% Experimental Glitter Interference Gold: similar effect as shown in example 1 except that the blue color from experimental glitter interference blue is more apparent.
16. 2% Reflecks™ Gleams of Gold/2% Experimental Glitter Interference Blue: the gold color dominates.
17. 2% Experimental Glitter interference Green/2% Reflecks™ Dimensions Sparkling Red: similar effect as described in example 1.

With respect to the preceding tables, the compositions of the various pigments are listed as follows:

| Description | INCI name | D50 (μm) | Particle Size Range (μm) |
|---|---|---|---|
| Colorona ® Glitter Copper | mica, iron oxides | 65~82 | 10~150 |
| Timiron ® Splendid Gold | titanium dioxide, mica, silica | 18~25 | 10~60 |
| Timiron ® Splendid Green | titanium dioxide, mica, silica | 18~25 | 10~60 |
| Xirona ® Magic Mauve | silica, titanium dioxide, tin oxide | 16~22 | 5~50 |
| Xirona ® Nordic Sunset | silica, titanium dioxide, tin oxide | 16~23 | 5~50 |
| Xirona ® Volcanic Fire | titanium dixodixe, silica, mica | 19~25 | 10~60 |
| Experimental Glitter Interference Blue | mica, titanium dioxide | 60~100 | 10~150 |
| Experimental Glitter Interference Gold | mica, titanium dioxide | 60~100 | 10~150 |
| Experimental Glitter Interference Green | mica, titanium dioxide | 60~100 | 10~150 |
| Experimental Glitter Interference Red | mica, titanium dioxide | 60~100 | 10~150 |
| Large particle size color travel (Green blue/Lilac) | mica, titanium dioxide, silica, tin oxide | ~85 | 10~150 |
| Large particle size color travel (Red/Gold) | mica, titanium dioxide, silica, tin oxide | ~85 | 10~150 |
| Reflecks ™ Beams of Blue | borosilicate, titanium dioxide | ~94 | 4~190 |
| Reflecks ™ Gleams of Gold | borosilicate, titanium dioxide | ~94 | 4~190 |
| Reflecks ™ Dimensions Sparkling Red | borosilicate, titanium dioxide | | 75~100 |

The entire disclosures of all applications, patents and publications, cited herein and of corresponding U.S. Provisional Application Ser. No. 60/606,503, filed Sep. 2, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of producing mixtures of interference pigments having special effects comprising mixing at least one glitter interference pigment having a particle size range of 10-150 μm and a particle size distribution $D_{50}$ of more than 40 μm with at least one interference pigment of predetermined colors having a particle size range of 10-60 μm and a particle size distribution $D_{50}$ of less than 40 μm wherein at least one glitter pigment has a complementary color to at least one interference pigment.

2. A mixture of pigments as obtaing by claim 1.

3. In a formulation that is cosmetics, personal care products, paints, coatings or printing inks containing a special effect pigment, the improvement wherein the special effect pigment is a mixture of pigments according to claim 2.

4. The formulation according to claim 3 containing absorbents, astringents, antimicrobial substances, antioxidants, antiperspirants, antifoaming agents, antidandruff active ingredients, antistatics, binders, biological additives, bleaching agents, chelating agents, deodorants, emollients, emulsifiers, emulsion stabilizers, dyes, fillers, humectants, film formers, odor substances, flavor substances, insect repellents, preservatives, anticorrosion agents, cosmetic oils, solvents, oxidants, vegetable constituents, buffer substances, reducing agents, surfactants, propellent gases, opacifiers, UV filters and UV absorbers, denaturing agents, viscosity regulators, perfume or vitamins.

5. The cosmetic and personal care products according to claim 3 which are lipophilic, hydrophilic or hydrophobic.

6. The method according to claim 1, wherein the $D_{50}$ value of the glitter interference pigment and the $D_{50}$ value of the interference pigment differ by 40-80 μm.

7. The pigment according to claim 2, wherein the $D_{50}$ value of the glitter interference pigment and the $D_{50}$ value of the interference pigment differ by 40-80 μm.

* * * * *